(12) United States Patent
Schroeder et al.

(10) Patent No.: US 8,564,768 B2
(45) Date of Patent: Oct. 22, 2013

(54) HIGH PRESSURE AND HIGH TEMPERATURE OPTICAL SPECTROSCOPY CELL USING SPHERICAL SURFACED LENSES IN DIRECT CONTACT WITH A FLUID PATHWAY

(75) Inventors: Robert Schroeder, Newtown, CT (US); Bill Grant, Cedar Creek, TX (US); Dan Angelescu, Noisy le Grand Cedex (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 512 days.

(21) Appl. No.: 12/642,385

(22) Filed: Dec. 18, 2009

(65) Prior Publication Data

US 2010/0265492 A1      Oct. 21, 2010

Related U.S. Application Data

(60) Provisional application No. 61/170,488, filed on Apr. 17, 2009.

(51) Int. Cl.
*G01N 1/10* (2006.01)
(52) U.S. Cl.
USPC .......................................... 356/246; 250/258
(58) Field of Classification Search
USPC ........... 356/244–246; 250/254, 255, 256, 258
See application file for complete search history.

(56) References Cited

U.S. PATENT DOCUMENTS 4,747,687 A * 5/1988 Hoppe et al. .................. 356/246
4,802,761 A * 2/1989 Bowen et al. ................. 356/301
5,046,854 A * 9/1991 Weller et al. .................. 356/440
5,054,919 A * 10/1991 Bryan ............................ 356/246
5,124,555 A * 6/1992 Hartl ............................. 250/373
5,274,227 A * 12/1993 Moring .................... 250/227.25
5,310,526 A * 5/1994 Yalvac et al. .................... 422/81
5,434,664 A * 7/1995 Sapp ............................. 356/244

(Continued)

FOREIGN PATENT DOCUMENTS

CA          2479695         9/2003
EP          0597552 A1      5/1994

(Continued)

OTHER PUBLICATIONS

Bacher et al, "Fabrication of LIGA mold inserts", Microsystem Technologies 4 (1998), pp. 117-119.

(Continued)

*Primary Examiner* — Tarifur Chowdhury
*Assistant Examiner* — Michael P LaPage
(74) *Attorney, Agent, or Firm* — Jakub Michna; Rachel E. Greene; Bridget Laffey

(57) ABSTRACT

Devices, methods and systems for making optical measurements of a fluid at elevated pressures and temperatures are disclosed. A cell is designed for the optical spectroscopic measurements of fluids or gas using light from ultra violet (UV) to far infrared wavelengths, among other wavelengths. A cell is described that is well suited for applications using very small fluid volumes, on the order of micro liters, such as microfluidic systems. Some described embodiments are suited for very high pressure and temperature environments (for example, 20 kpsi or greater at 175 degree C. or greater). Such conditions, for example, may be found in oilfield downhole environments. Some embodiments provide are inexpensive, and make use of replaceable lenses that are used as a pressure barrier and for collimation of the optical beam path for spectroscopic measurements.

48 Claims, 6 Drawing Sheets

(56) References Cited

U.S. PATENT DOCUMENTS

| | | | |
|---|---|---|---|
| 5,923,431 A * | 7/1999 | Masterson et al. | 356/426 |
| 6,281,975 B1 * | 8/2001 | Munk | 356/440 |
| 6,474,152 B1 | 11/2002 | Mullins et al. | |
| 6,638,668 B2 | 10/2003 | Buchsbaum et al. | |
| 6,700,690 B1 | 3/2004 | Buchsbaum et al. | |
| 6,839,176 B2 | 1/2005 | Buchsbaum et al. | |
| 7,149,033 B2 | 12/2006 | Buchsbaum | |
| 7,515,259 B2 | 4/2009 | Hilmer et al. | |
| 7,575,681 B2 | 8/2009 | Angelescu et al. | |
| 7,695,629 B2 | 4/2010 | Salamitou et al. | |
| 7,799,278 B2 | 9/2010 | Salamitou et al. | |
| 8,262,909 B2 | 9/2012 | Angelescu et al. | |
| 2003/0036206 A1 * | 2/2003 | Chien et al. | 436/180 |
| 2005/0063869 A1 | 3/2005 | Follonier et al. | |
| 2007/0064226 A1 | 3/2007 | Kolp et al. | |
| 2007/0211244 A1 | 9/2007 | Hilmer et al. | |
| 2008/0173805 A1 | 7/2008 | Indo et al. | |
| 2008/0307860 A1 | 12/2008 | Guieze et al. | |
| 2010/0041155 A1 | 2/2010 | Angelescu et al. | |

FOREIGN PATENT DOCUMENTS

| | | |
|---|---|---|
| JP | H01075851 | 3/1989 |
| JP | H02042337 | 2/1990 |
| JP | H04309843 | 11/1992 |
| JP | H09264840 | 10/1997 |
| JP | 11-173975 A | 7/1999 |
| JP | 2000-218797 A | 8/2000 |
| JP | 2002220989 | 8/2002 |
| JP | 2002267596 | 9/2002 |
| JP | 2003279471 | 10/2003 |
| JP | 2004157043 | 6/2004 |
| JP | 2005329330 | 12/2005 |
| JP | 2007506978 | 3/2007 |
| JP | 2008-216094 A | 9/2008 |

OTHER PUBLICATIONS

Daniel Harris, Infrared Window and Dome Materials, "Design of circular windows", Section 2.2.5, pp. 62-64.

Muhlberger et al, "Microfluidic polyether ether keton (PEEK) chips combined with contactless conductivity detection for uTAS", 9th International Conference on Miniaturized Systems for Chemistry and Life Sciences, Oct. 9-13, 2005, Boston, Massachusetts, pp. 184-186.

Extended European Search Report of European Application No. 10764924.6 dated Aug. 29, 2012: pp. 1-8.

Ocean Optics Web Pages, 2007: pp. 1-14.

Office Action of Japanese Application No. 2012-503782 dated May 7, 2013: pp. 1-2.

* cited by examiner

HIGH PRESSURE AND HIGH TEMPERATURE OPTICAL SPECTROSCOPY CELL USING SPHERICAL SURFACED LENSES IN DIRECT CONTACT WITH A FLUID PATHWAY

CROSS REFERENCE TO RELATED APPLICATION

This patent application claims benefit of U.S. Provisional Patent Application Ser. No. 61/170,488, filed Apr. 17, 2009 which is incorporated by reference herein.

BACKGROUND

1. Field of the Subject Matter Disclosed

The subject matter disclosed in the application generally relates to devices and methods for integration of optical sensors with microfluidic systems. In particular, the integration of one or more fiber as a feed through into a microfluidic cell such as a high pressure and/or high temperature microfluidic cell, that provides optical signal throughput, a collimated light path for spectroscopy and provides for minimum sized fluid dead volumes for microfluidic applications.

2. Background of the Subject Matter Disclosed

Often in many applications there is a need for transmitting optical signal from one side of a metallic part to the other, for example, measuring fluid and gas analysis. Often, such transmission needs to occur while there is a significant pressure difference between the two sides of the metallic part. Several solutions exist to this problem, including but not limited to the use of optical windows sealed with elastomeric o-rings or brazed to the metallic part.

In many applications there is also a need for a metallic part with very intricate details machined in it, such as small channels and holes, at length scales and resolutions down to the micron level, which are not easily achievable using conventional machining techniques. One example of a situation where such a need exists is in the manufacturing of metallic microfluidic devices.

Accordingly, there is a need for improved methods and systems capable of providing devices worthy of use in demanding environments so as to withstand, by non-limiting example, high pressures, high temperatures and harsh environments. There is also the need for versatile fabrication methods for integrating optical sensors with microfluidic systems capable of manufacturing and/or processing of parts having characteristics, such as: high structural strength and excellent chemical resistance.

SUMMARY OF THE SUBJECT MATTER DISCLOSED

According to some embodiments, a cell designed for the optical spectroscopic measurements of fluids or gas is provided. It is noted that some embodiments of the subject matter disclosed in the application can provide for a cell that can be used from ultra violet (UV) to far infrared wavelengths, among other wavelengths. According to some embodiments, devices capable of measurements made similar to Schlumberger's DFA suite (LFA, CFA, pH). According to some embodiments, a cell is provided that is well suited for applications using very small fluid volumes, on the order of micro liters, such as microfluidic systems. Some embodiments are suited to larger volumes. At least some embodiments are particularly useful in very high pressure and temperature environments (for example, 20 kpsi or greater at 175 degree C. or greater). Such conditions, for example, may be found in oilfield downhole environments. However, it is conceived that some embodiments may be used for surface and subterranean environments. It is noted that some embodiments of the subject matter disclosed in the application can be used for H2S and CO2 environments.

According to some embodiments, the design is simple, of very small size, by non-limiting example, less than 1 inch×1 inch×0.5 inch, uses inexpensive, replaceable lenses that provide the pressure barrier and collimation of the optical beam path for spectroscopic measurements. Further, some embodiments can provide for modularity in design, allowing single fiber ports on either side, or a combination of optical single fiber and/or photodiodes, light emitting diodes, small tungsten halogen lamps. Further still, some embodiments can be used as a replacement for the DFA optical cell presently in use, thereby using a small physical space even in non-microfluidic applications. According to some embodiments, a cell is provided that operates at up to 20 Kpsi at 175 C, with excellent optical performance over that of known similar devices. According to at least one embodiment, a design is provided that retains up to 40 kpsi of pressure and greater.

According to at least one embodiment, a metal is grown around one or more lens or windows so as to replace sealing devices such as O-rings, or the like. According to some embodiments a method of brazing may be utilized to braze Sapphire metal parts to an O-ring. According to some embodiments, materials such as Sapphire and/or diamonds are used. According to some embodiments, Quartz is a material used, which can result in a larger sized device due to reduced pressure strength properties.

According to some embodiments, the lens may be adjustable when positioned in the device. Further, the lens shape may be non-uniformly or uniformly spherical shaped, having at least one side that is non-uniformly or uniformly spherical shaped.

Further features and advantages of the subject matter disclosed in the application will become more readily apparent from the following detailed description when taken in conjunction with the accompanying drawings.

BRIEF DESCRIPTION OF THE DRAWINGS

The subject matter disclosed in the application is further described in the detailed description which follows, in reference to the noted plurality of drawings by way of non-limiting examples of exemplary embodiments of the subject matter disclosed in the application, in which like reference numerals represent similar parts throughout the several views of the drawings, and wherein.

DETAILED DESCRIPTION OF THE PREFERRED EMBODIMENTS

Figure 1A:
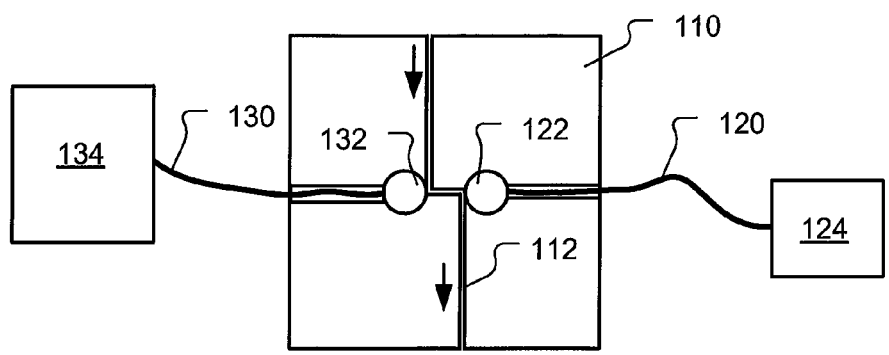
FIGS. 1a, 1b and 1c are schematics illustrating high pressure and/or high temperature microfluidic optical cell, according to some embodiments.

The particulars shown herein are by way of example and for purposes of illustrative discussion of the embodiments of the subject matter disclosed in the application only and are presented in the cause of providing what is believed to be the most useful and readily understood description of the principles and conceptual aspects of the subject matter disclosed in the application. In this regard, no attempt is made to show structural details of the subject matter disclosed in the application in more detail than is necessary for the fundamental understanding of the subject matter disclosed in the application, the description taken with the drawings making apparent to those skilled in the art how the several forms of the subject matter disclosed in the application may be embodied in practice. Further, like reference numbers and designations in the various drawings indicated like elements.

According to some embodiments, at least one optical sensor is integrated with a microfluidic system. Current systems for downhole optical spectroscopy, for example with Schlumberger's MDT product line, can be performed with two large diameter (approximately 5 mm) fiber bundles. In the case of the MDT product line, the fiber bundles are positioned on opposing sides of two, 7 mm thick, 6 mm diameter sapphire pressure windows. Each fiber bundle consists hundreds of single multimode fibers. The gap between the two sapphire windows, the optical path length, is about 2 mm. One fiber bundle provides illumination from a tungsten halogen lamp. The second fiber bundle collects light after it has transverse the multiphase fluids in the MDT flowline. Note that in current system, the light path from the fibers is commonly transverse to the flow direction. Each individual fiber in the fiber bundle expands or collects light within it numerical aperture (n.a.). Numerical aperture is defined as $n.a.=n_m \sin(\theta)$, where $\theta$ is the half angle of light emission/collection from the fiber and $n_m$ is the medium (fluid or air) that the fiber's distal end is immersed in.

Currently available systems, such as with Schlumberger's MDT product line, typically use relatively large flow volumes and cross sections. Cross sections are measured in millimeters. In contrast, in microfluidics applications, the flow volumes are measured in micro liters and cross sections of microfluidic flow systems are 10 to several hundreds of microns. As used herein the term "microfluidic" means a system having a flowpath having a cross section less than about 1 mm. The common range for cross sectional dimensions in microfluidic pathways is about a few 10s of microns to several 100s of microns.

The integration of optics into microfluidic flow systems was first developed as a pH Diver Tool for Schlumberger Water Services. See, U.S. Pat. No. 7,799,278, which is incorporated herein by reference. The pH Diver was a complete Lab-on-Chip tool for low temperature and pressure service (less than 50 C and a 1000 psi of pressure). The pH chip had an optical cell channel that measured 10 mm long by 130 micron square. Single optical fibers where integrated into the plastic (COC) chip of approximately the same dimension (125 micron diameter fiber). The fibers where glued into a COC pocket and behind a transparent COC window that kept fluids out of contact with the fiber surface. Since no focusing optics were integrated with the pH chip, light expanded within the n.a. of the single fiber before reaching the collection fiber 10 mm away. This simple, low cost designed works very well for the intended applications, but the light loss was approximately 18 dB or a factor of 60 due to the lack of light collimation.

Optical fibers can epoxied within a metal (e.g. stainless steel) tube and the tube sealed with HIP pressure fittings into either end of a microfluidic flow system. The shear strength of the epoxy provides the pressure barrier between the fiber and the stainless steel tube. However, problems can arise with the use of epoxy when operating at high temperatures. According to some embodiments, optical fibers (e.g. quartz or sapphire) could be mounted or sealed via metal (e.g. nickel) vapor deposition growth around the fibers directly or tube containing the fibers. For further details on such growth techniques, see Angelescu and Schroeder, 'Fabrication Technique for Metallic Devices with Embedded Optical Elements, Optical devices, or Optical and Electrical Feedthroughs', U.S. Pat. No. 8,389,054, issued on Mar. 5, 2013, hereinafter referred to as the "'504 patent ", which is hereby incorporated by reference herein. In systems within out a lens or a pressure window, the HPHT fluid contact with the epoxy or the fibers themselves can be a failure point. Also, in systems without lenses, even though the light emitted by the fibers will reflect off of the metal walls inside the fluidic device (unlike the pH transparent COC chip), there is no real optical gain from that process, due to the large reflection losses in the metal. Thus, according to some embodiments, a lens that acts as a pressure window is provided that results in improved optical signal throughput, gives a collimated light path for spectroscopy and maintains very small fluid dead volumes for microfluidic applications. According to some other embodiments a separate pressure window and lens are provided.

Figure 1B:
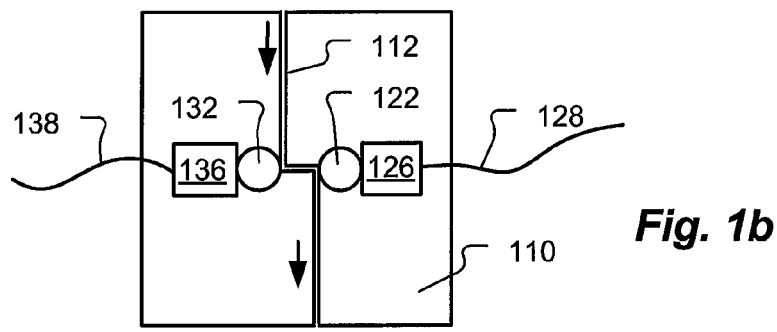
Figure 1C:
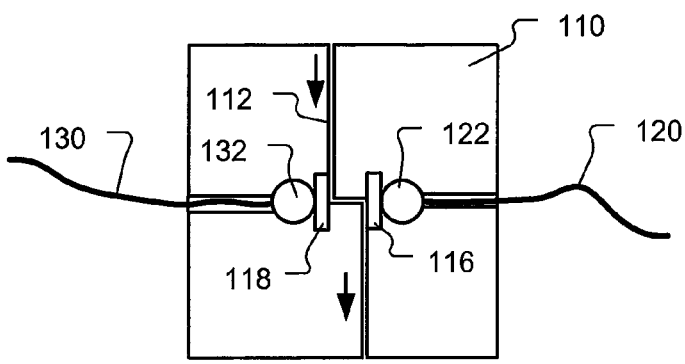

FIGS. 1*a*, 1*b* and 1*c* are schematics illustrating high pressure and/or high temperature microfluidic optical cell, according to some embodiments. As used herein the term high pressure and/or high temperature (HPHT) means above 1 kpsi and above 50 C, although some embodiments described herein are capable of safely operating at 20 kpsi at 185 C. Further, some embodiments described herein are further capable of operating at 40 kpsi at 225 C. In FIG. 1*a*, microfluidic optical cell 110 is made from metal (nickel, SS, etc). A microfluidic pathway 112 is formed within the body of cell 110. Note that although the pathway is shown parallel to the optical measurement path, other arrangements are possible according to other embodiments. Also, although liquids such as oilfield liquids may be discussed in connection with various embodiments, the pathway 112 and similar pathways described herein can be used to carry and optically analyze gases as well. Optical lenses 122 and 132 are sealed in place along the pathway 112 so as to maintain a high pressure seal in pathway 112. The lenses 122 and 132 provide a collimated light path for spectroscopy though pathway 112, thereby providing improved optical signal throughput. Optical fibers 120 and 130 are optically coupled to lenses 122 and 132 respectively. Fiber 120 carries light from light source 124 to lens 122, and fiber 130 carries light from lens 130 to optical detector 134. Note that although only a single fibers 120 and 130 are shown on either side of cell 110, according to other embodiments, other numbers of fibers can be used.

FIGS. 1*b* and 1*c* show an arrangement according to some other embodiments. In FIG. 1*b*, the lens 122 is coupled directly with a light source 126, which is preferably a point source of light such as an LED. Likewise, lens 132 is coupled directly with a photodetector 136 such as a photodiode. Electrical signals are carried to the source 126 and from the detector 136 via wires 128 and 138 respectively. In FIG. 1*c*, separate pressure windows 116 and 118 provide high pressure sealing along pathway 112. Note that according to different embodiments, different combinations of optical fibers, direct couplings of sources and detectors, and separate pressure windows are provided using the arrangements shown in FIGS. 1*a-c*. Note that with the use of collimating lenses, the light sources used are preferably point light sources such as LEDs. As used herein the term "point source" of light refers to a light source whose light emitting portion has a physical extent on the order of 10s to 100s of microns, and when placed at the focal point of a lens, tends to produce collimated light essentially parallel to the optical axis of the lens system.

Figure 2A:
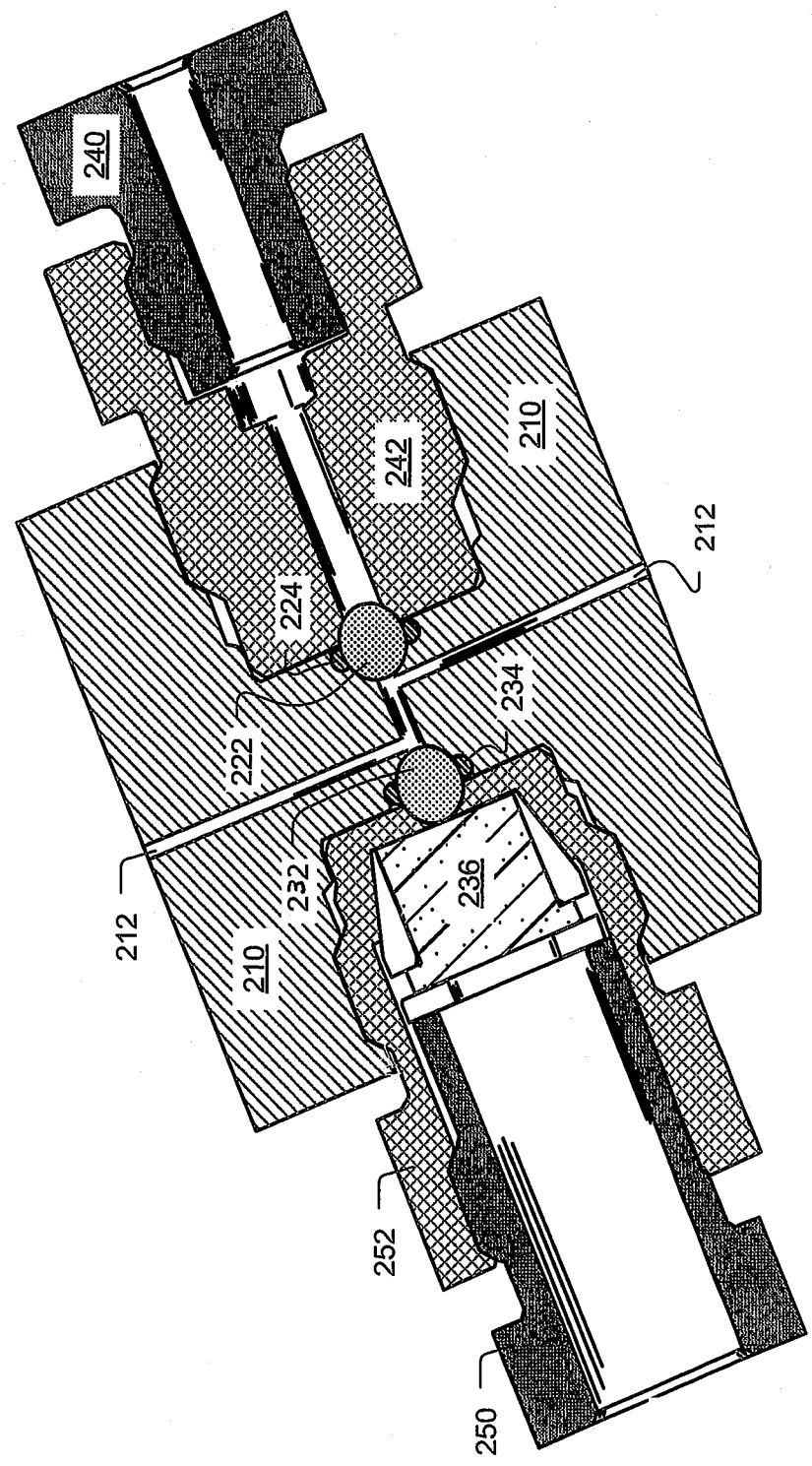
FIG. 2a shows a modularly designed high pressure high temperature microfluidic optical cell, according to some embodiments.

FIG. 2a shows a modularly designed high pressure high temperature microfluidic optical cell, according to some embodiments. In particular, FIG. 2a shows the main cell block 210 that is made from titanium and measures about 1 inch×0.6 inch×0.5 inch in dimension. The two 2 mm sapphire ball lenses 222 and 232 are shown, along with the sealing Viton o-rings 224 and 234. The lenses 222 and 232 are held in place with lens retainers 242 and 252 respectively. On the right side is shown a retaining nut 240 for a small sized (mu type) fiber ferrule holding a 100 micron core fiber. The left side retaining nut 250, according to some embodiments, holds a second mu fiber ferrule. However, in the embodiment shown in FIG. 2a, a photodiode 236 is mounted instead. According to some other embodiments, the unit 236 is an LED light source. It will be recognized that other options are also possible according to other embodiments.

It has been found that, arrangements such as shown in FIG. 2a are able to operate at pressures of up to 20 kpsi at 175 C with no fluid leaks. It has also been found that the optical spectrum of such arrangements compare well with a baseline laboratory spectrometer. Other metrological tests have been performed indicating that embodiments of the subject matter disclosed in the application are able to handle even higher pressures than 20 kpsi and at higher temperatures than 175 C without fluid leaks.

According to some embodiments, novel methods and devices are provided that transfer light from a single optical fiber, through a high pressure and high temperature (e.g. 20 kpsi at 175 C) fluid or gas to a receiving single optical fiber or photodiode. Among other things, some embodiments are particularly suited for small volume microfluidic systems that require optical integration. However, according to some embodiments, arrangements for larger volume sample systems are also provided.

Because microfluidic environments involve very small cross sectional channels, the combination of the material strength of sapphire, among other materials, and the small exposed area allows for very thin pressure windows. According to some embodiment such as shown in FIG. 1c, a small planar sapphire window is used for pressure retention, behind which was placed a lens (of any material, like fused silica) for beam collimation from an optical fiber or other source, such as a light emitting diode (LED). A receiving window and lens combination provide the same function on the opposing end of the cell, but instead focuses the collimated light into a fiber or photodiode.

Figure 2B:
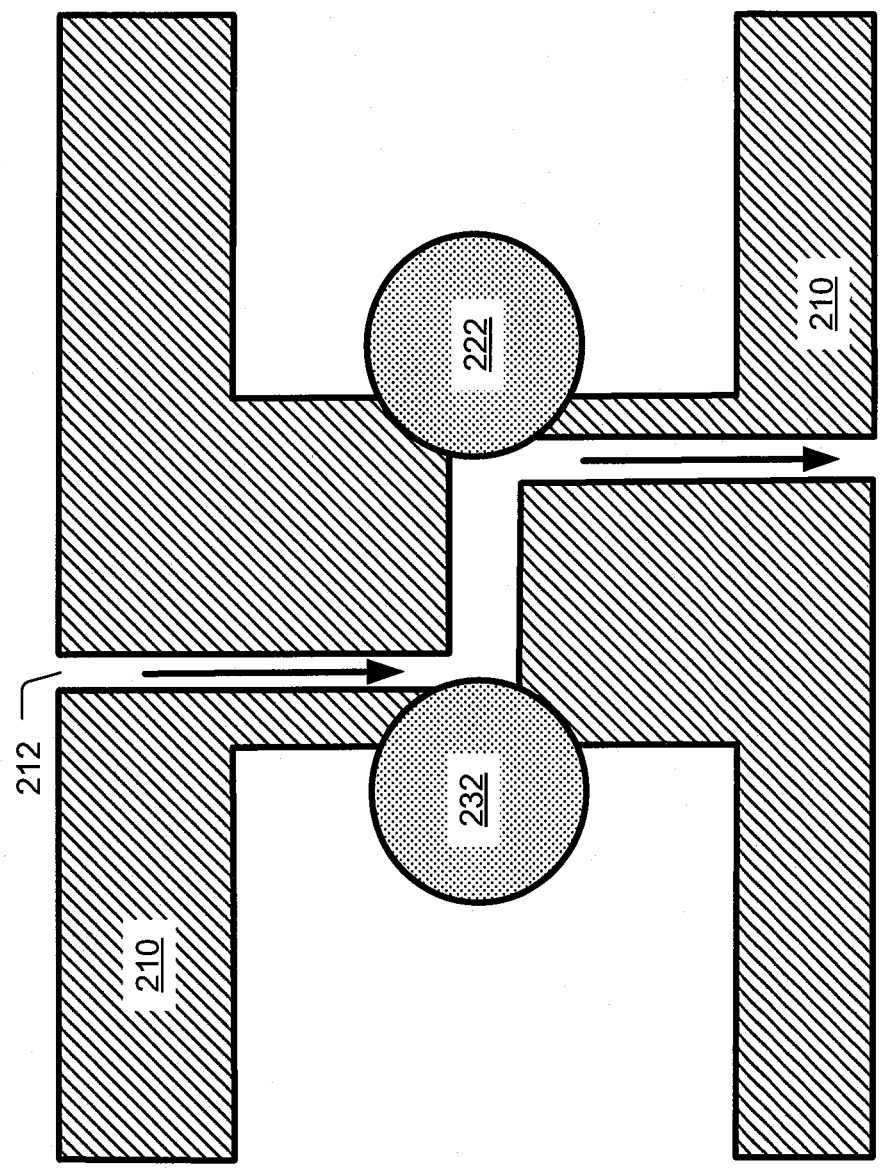
FIG. 2b shows a simplified view of the fluid path, according to some embodiments.

Sapphire, being robust to chemical attack and with a material strength of approximately 400 MPa has been found to be a good choice for the pressure windows, or the lenses, where not separate pressure window is provided. However, according to other embodiments, other materials having similar properties as Sapphire are be used. For example, $SiO_2$ or fused silica windows have only a strength of 60 MPa and could be used with sufficient thickness for a given application. In a planar window design, with only 600 microns diameter channel, a 1 mm thick sapphire window can be sufficient to hold off 20 kpsi of pressure with a safety factor of approximately 4 included. It has been found that minimizing the window diameter and still providing a seal (via an o-ring or metal sapphire brazing) will minimize the fluid dead volume. A larger diameter window is easy to seal, but will give larger dead volumes between the window and the o-ring. Further, by integrating the window and the lens in to a single part, it has been found that the fluid dead volumes can be reduced. Smaller fluid dead volumes are preferred for many microfluidic measurements. FIG. 2b shows a simplified view of the fluid path, according to some embodiments. The fluid takes a Z-shaped path along fluid pathway 212. To conform to measurement standard for existing tool systems, a predetermined optical path length may be highly desirable, the Z-path is a useful way to obtain such path lengths for microfluidic systems. For example, for Schlumberger's MDT tools using DFA, the standard optical cell path length is approximately 2 mm. To achieve this with a 600 micron diameter fluid path, the cell design directs the light path in line with the fluid flow. This is different than the current DFA design, but has been found to be of little optical significance.

The complication of mounting the window can be compounded by the need to also mount an additional focusing lens and the small optical fiber behind it. Given the small maximum optical beam diameter required (<0.6 mm), the off-the-shelf availability of sapphire lenses (in particular spherical or ball designs), combining the functionality of the lens and window has been found to be advantageous.

Figure 3A:
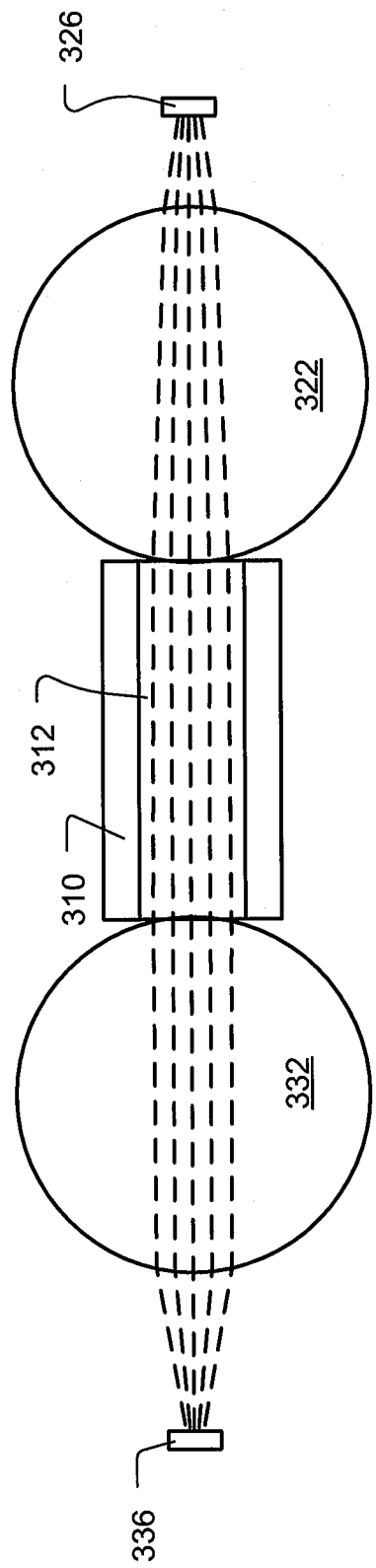
FIGS. 3a and 3b show examples of results an optical ray trace model of an arrangement according to some embodiments.
Figure 3B:
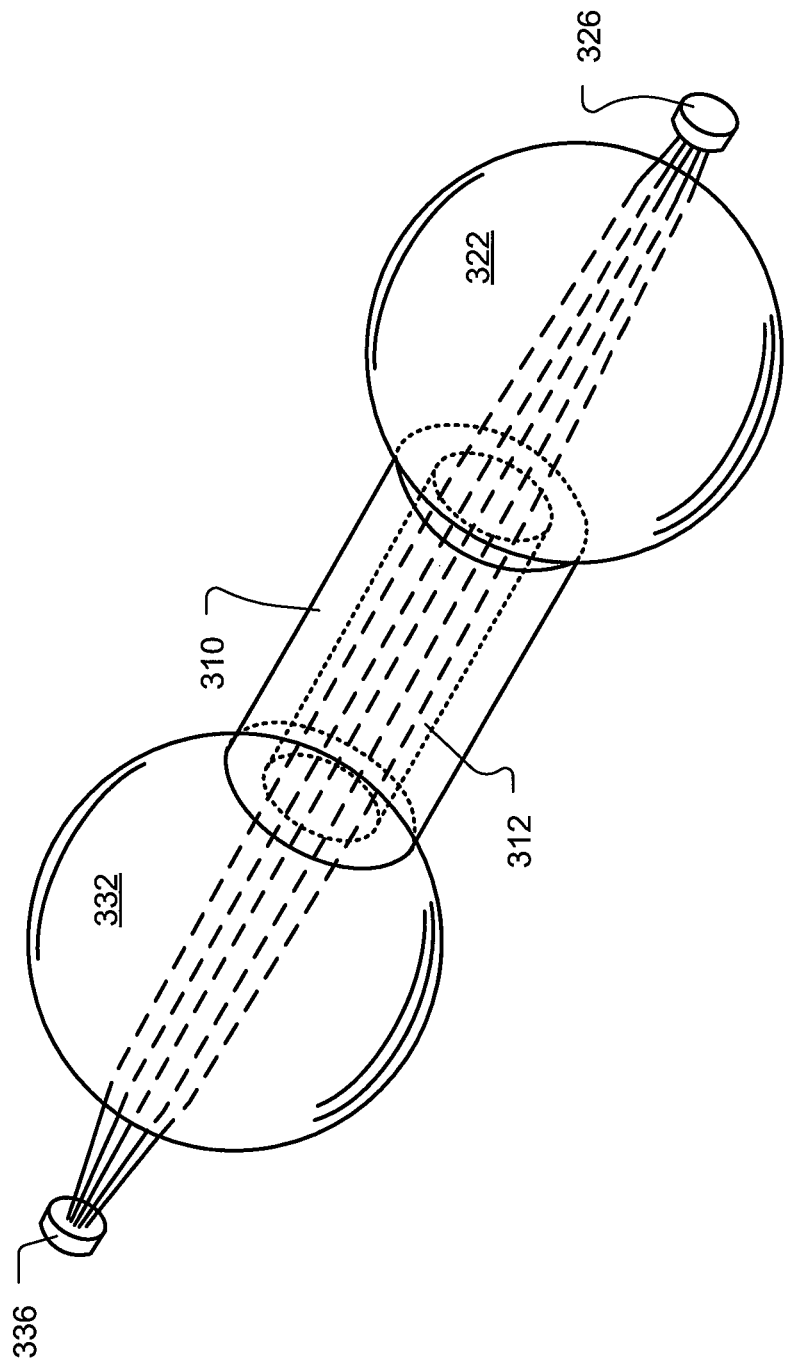

FIGS. 3a and 3b show examples of results for an optical ray trace model of an arrangement according to some embodiments, made with commercial software (TracePro® from Lambda Research Corp.) 2 mm ball lens 322 and 332 are immersed on one side with oil or water, as is shown. By adjustment of the locations of the emitting source 336 and the receiving fiber 326, to compensate for fluid immersion of the two ball lenses 322 and 332, optical beam collimation can be achieved within pathway 312 defined by wall 310. Collimation of the interrogation light source is ideal for spectroscopic measurements. It has been found that the arrangement shown makes for a very simple robust design. According to some embodiments, other sizes and shapes of lenses are used, depending on the optical design, the anticipated pressures, and the sealing technology.

The ball lenses 322 and 332 can be sealed with small o-rings or brazed into retaining pockets (not shown). To make the mechanical sealing easier, 2 mm diameter ball lenses (cost: $12 each) are used, according to some embodiments. It has been found that with an exposed diameter of only 0.6 mm, the strength of sapphire will retain up to 40 kpsi of pressure.

Figure 4:
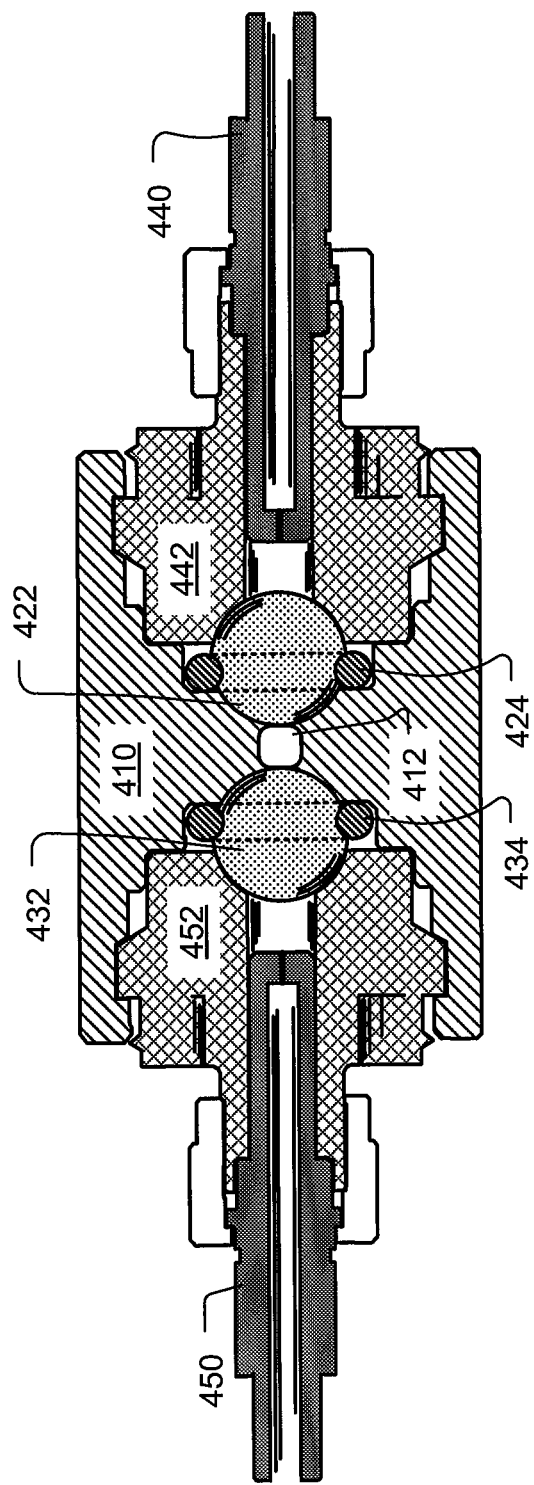
FIG. 4 shows a high pressure high temperature optical cell, according to some embodiments.

FIG. 4 shows a high pressure high temperature optical cell, according to some embodiments. The cell shown in FIG. 4 is designed to operate at high pressures and high temperatures of extreme environments, such as in subterranean locations. According to some embodiments, the single lens/window design described herein is used in non-microfludic applications as well. While many of the embodiments described herein are particularly well suited for downhole deployment due to their small size, robust design and HPHT capabilities, many of the embodiments are also suitable for analysis on the surface where HPHT cells are used, such as measurement of dew point, bubble point, spectroscopy and other optical measurements. Additionally some of the non-microfluidic embodiments are well suited to multiphase flow analysis as well. Two ball lenses 422 and 432, approximately 6 mm diameter each, and a single fiber on either end is used instead of a pressure window and large bundles of fibers as in conventional cells. The ball lenses 422 and 432 are sealed onto the flow line 412 within body 410 using o-rings 424 and 434 respectively. The flow line 412 is approximately 2 mm in diameter and the flow is transverse to the optical path as shown. The lenses 422 and 432 are held in place using lens retainers 442 and 452 respectively. Fiber ferrules are held on either side of the cell with retainers 440 and 450. Note that according to some embodiments, two or more fibers are used. Further, according to some embodiments of the subject matter disclosed in the application, the lens is mounted on the flowline of a tool such as Schlumberger's MDT tool line, like a ball filling the holes of a flute.

Advantages of embodiments such as shown in FIG. 4 include the small size of the parts and mounting hardware, and the smaller bend radius of the single fiber vs. the stiffer fiber bundle. Additionally, with the use of collimating lenses 422 and 432, all the light from the single fiber is imaged through the flow line, whereas in conventional arrangements without lenses not all fibers 'see' the same flow regime per unit of time measurement.

According to some embodiments, the arrangements described herein a may be used in accordance with the '054 patent, which describes methods for fabricating devices having embedded features such as optical devices. It is noted that some embodiments may include one or more topographical patterns of a base substrate, along with other devices such as: an optical element, an optical device, a portion of a channel, an enclosed channel, an optical feedthrough, an electrical feedthrough, a sensor device, a wire shaped device or some combination thereof.

According to some embodiments, the arrangements described herein may be used in accordance with U.S. Pat. No. 7,799,278 to Salamitou et al., incorporated by reference herein in its entirety, which discloses the use of self-supporting microfluidic systems for chemical analysis of water or mixtures of water and oil.

According to some embodiments, a small ball lens is used that holds off enough pressure for a microfluidic device, wherein a material such as nickel is grown around the lens. This material growing technique on the lens or window has been found to be effective in reducing the fluid dead volume in some embodiments. According to some embodiments, the microchannel having a cross section of about 140 microns is exposed to pressures of up to 20 kpsi. The thickness sapphire is about 80 micron, and if fused silica is used instead of sapphire the thickness is about 200 microns. It is noted these dimensions include a safety margin of approximately 4. According to some embodiments a 300 micron ball lens has been found to be adequate to provide an adequate pressure barrier up to at least 20 Kpsi and some degree of collimation of light to improve throughput.

The strength S of materials used is 60 MPa for fused silica and 400 MPa for sapphire. The following formula can be used:

$$d/L = 0.5 \mathrm{sqrt}\{k*f*P/S\}$$

where f=4 is the safety factor, P is pressure in MPa, k varies between 0.75 and 1.125 depending on whether the window is secured on one or both sides to pressure, and d/L is the ratio of window thickness/exposed window diameter, (see data and formula from: Infrared Window and Dome Materials, Daniel C. Harris, Tutorial Texts in Optical Engineering, Vol. TT10, SPIE Optical Engineering Press, 1992, which is incorporated by reference herein.)

Although the techniques described herein can be used for optical measurements in multiphase flow, it has been found that many of the microfluidic embodiments are particularly well suited for optical measurements for single phases.

Several embodiments of the subject matter disclosed in the application have been described. Nevertheless, it will be understood that various modifications may be made without departing from the spirit and scope of the subject matter disclosed in the application. For example, embodiments of the subject matter disclosed in the application as disclosed above have many further applications in both surface and subterranean environments, such as reducing the size of spectroscopic measurements and/or being a part of new optical measurements under HPHT conditions. It is noted that the foregoing examples have been provided merely for the purpose of explanation and are in no way to be construed as limiting of the subject matter disclosed in the application. While the subject matter disclosed in the application has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the subject matter disclosed in the application in its aspects. Although the subject matter disclosed in the application has been described herein with reference to particular means, materials and embodiments, the subject matter disclosed in the application is not intended to be limited to the particulars disclosed herein; rather, the subject matter disclosed in the application extends to all functionally equivalent structures, methods and uses, such as are within the scope of the appended claims.

What is claimed is:

1. A device for making optical measurements of a fluid at elevated pressures and temperatures, the device comprising:
   a body comprising a fluid pathway;
   a source of light;
   a light detector;
   a first lens in optical in communication with the source of light, wherein the first lens includes a spherical surface that is exposed to fluid in the fluid pathway and the first lens collimates light from the source and directs the light through the fluid pathway;
   a first sealing ring in contact with the spherical surface of the first lens to generate a seal between the first lens and the body;
   a first retainer for holding the first lens in place;
   a second lens in optical communication with a light detector, wherein the second lens includes a spherical surface that is exposed to fluid in the fluid pathway and the second lens directs the collimated light from the fluid pathway towards the light detector;
   a second sealing ring in contact with the spherical surface of the second lens to generate a seal between the second lens and the body; and
   a second retainer for holding the second lens in place.

2. The device according to claim 1, wherein the pathway is a microfluidic pathway.

3. The device according to claim 1, wherein the first and second lenses are made from sapphire.

4. The device according to claim 1, wherein the first and second lenses are spherical shaped.

5. The device according to claim 1, wherein the source of light is a point source of light.

6. The device according to claim 5, wherein the light emitting area of the point source of light has a largest physical dimension of less than 500 microns.

7. The device according to claim 1, further comprising a first optical fiber adapted and positioned so as to transmit light from the source of light to the first lens.

8. The device according to claim 7, wherein predominantly all of the light that the first lens receives from the source of light is transmitted through the first optical fiber.

9. The device according to claim 1, further comprising a second optical fiber adapted and positioned so as to transmit light from the second lens to the light detector.

10. The device according to claim 9, wherein predominantly all of the light that the light detector receives from the second lens is transmitted through the second optical fiber.

11. The device according to claim 1, wherein the light source is either a light emitting diode or a tungsten halogen lamp.

12. The device according to claim 11, wherein the light source is a light emitting diode and is positioned so as to directly emit light into the first lens.

13. The device according to claim 1, wherein the light detector is a photodiode.

14. The device according to claim 13, wherein the photodiode is positioned proximately to the second lens so as to receive light directly from the second lens.

15. The device according to claim 1, wherein the first lens is dimensioned, shaped, and positioned such that the light directed through the fluid pathway predominantly travels parallel to a main axis of the first lens.

16. The device according to claim 1, wherein the device is designed so as to operate at pressures within the pathway of at least 5 kpsi.

17. The device according to claim 16, wherein the device is designed so as to operate at pressures within the pathway of at least 10 kpsi.

18. The device according to claim 17, wherein the device is designed so as to operate at pressures within the pathway of at least 20 kpsi.

19. The device according to claim 1, wherein the device is designed so as to operate at temperatures of at least 50 C.

20. The device according to claim 1, wherein the device is designed so as to operate at temperatures of at least 175 C.

21. The device according to claim 1, wherein light emitted from the source and detected by the detector includes wavelengths predominantly within a range consisting of ultraviolet and far infrared wavelengths.

22. The device according to claim 1, wherein the optical measurements are spectroscopic measurements.

23. The device of claim 1, wherein the first sealing ring and the second sealing ring are o-rings.

24. The device of claim 1, wherein the body of the device comprises a metal material.

25. The device of claim 1, wherein the collimated light from the first lens travels toward the second lens in a direction approximately parallel to fluid flow in the fluid pathway.

26. A method for making optical measurements of a fluid at elevated pressures and temperatures, the method comprising:
deploying an optical cell downhole;
flowing a fluid into a fluid pathway within a body of the optical cell;
generating light from a source of light;
collimating light from the source using a first lens and directing the light through the fluid pathway using the first lens, wherein the first lens includes a spherical surface that is exposed to fluid in the fluid pathway and the optical cell includes a first sealing ring in contact with the spherical surface of the first lens to generate a seal between the first lens and the body of the optical cell;
directing the collimated light from the fluid pathway with a second lens towards a light detector, wherein the second lens includes a spherical surface that is exposed to fluid in the fluid pathway and the optical cell includes a second sealing ring in contact with the spherical surface of the second lens to generate a seal between the second lens and the body of the optical cell; and
detecting light to make optical measurements of the fluid.

27. The method according to claim 26, wherein the pathway is a microfluidic pathway.

28. The method according to claim 26, wherein the first and second lenses are made from sapphire.

29. The method according to claim 26, wherein the first and second lenses are spherical shaped.

30. The method according to claim 26, wherein the source of light is a point source of light having a light emitting area with a largest physical dimension of less than 500 microns.

31. The method according to claim 26, further comprising a first optical fiber adapted and positioned so as to transmit light from the source of light to the first lens.

32. The method according to claim 31, wherein predominantly all of the light that the first lens receives from the source of light is transmitted through the first optical fiber.

33. The method according to claim 26, further comprising a second optical fiber adapted and positioned so as to transmit light from the second lens to the light detector.

34. The method according to claim 33, wherein predominantly all of the light that the light detector receives from the second lens is transmitted through the second optical fiber.

35. The method according to claim 26, wherein the light source is either a light emitting diode or a tungsten halogen lamp.

36. The method according to claim 35, wherein the light source is a light emitting diode and is positioned so as to directly emit light into the first lens.

37. The method according to claim 26, wherein the light detector is a photodiode.

38. The method according to claim 37, wherein the photodiode is positioned proximately to the second lens so as to receive light directly from the second lens.

39. The method according to claim 26, wherein the first lens is dimensioned, shaped, and positioned such that the light directed through the fluid pathway predominantly travels parallel to a main axis of the first lens.

40. The method according to claim 26, wherein the fluid pathway is designed to maintain pressures of at least 5 kpsi.

41. The method according to claim 40, wherein the fluid pathway is designed to maintain pressures of at least 10 kpsi.

42. The method according to claim 41, wherein the fluid pathway is designed to maintain pressures of at least 20 kpsi.

43. The method according to claim 26, wherein measurements are made while the fluid temperature is at least 50 C.

44. The method according to claim 43, wherein measurements are made while the fluid temperature is at least 175 C.

45. The method according to claim 26, wherein the generated light and the detected light includes wavelengths predominantly within a range consisting of ultraviolet and far infrared wavelengths.

46. The method of claim 26, wherein the body of the optical cell comprises a metal material.

47. The method of claim 26, wherein the first sealing ring and the second sealing ring are o-rings.

48. The method of claim 26, wherein the collimated light from the first lens travels toward the second lens in a direction approximately parallel to fluid flow in the fluid pathway.

* * * * *